United States Patent [19]

Deckner et al.

[11] Patent Number: 4,908,035
[45] Date of Patent: Mar. 13, 1990

[54] PROSTHESIS FOR A HIP JOINT

[75] Inventors: Andre G. Deckner, Paris, France; Martin Imhof, Rotkreuz, Switzerland; Karl Zweymuller, Vienna, Austria

[73] Assignee: Sulzer Brothers Limited, Winterthur, Switzerland

[21] Appl. No.: 262,882

[22] Filed: Oct. 26, 1988

Related U.S. Application Data

[63] Continuation of Ser. No. 32,329, Mar. 30, 1987, abandoned.

[30] Foreign Application Priority Data

Apr. 3, 1986 [CH] Switzerland ................... 1302/86-2

[51] Int. Cl.$^4$ ............................................. A61F 2/34
[52] U.S. Cl. ..................................................... 623/23
[58] Field of Search ................................... 623/22, 23

[56] References Cited

U.S. PATENT DOCUMENTS

| | | | |
|---|---|---|---|
| 3,939,498 | 2/1976 | Lee et al. | 623/23 |
| 4,004,300 | 1/1977 | English | 623/23 |
| 4,310,931 | 1/1982 | Muller | 623/23 |
| 4,359,785 | 11/1982 | Niederer | 623/23 |
| 4,422,187 | 12/1983 | Zweymuller | 623/23 |
| 4,516,277 | 5/1985 | Butel | 623/23 |
| 4,636,219 | 1/1987 | Pratt et al. | 623/22 |

Primary Examiner—Richard J. Apley
Assistant Examiner—David J. Isabella
Attorney, Agent, or Firm—Kenyon & Kenyon

[57] ABSTRACT

The prosthesis is provided with a medial narrow side which extends on a hyperbola from a conical distal section to a boundary plane at which the blade is connected to the neck of the prosthesis. The vertex of the hyperbola is disposed at the point of intersection of the curved medial narrow side with the neck and a tangent to the hyperbola at the point of intersection with the distal section is one-half the conical angle of the blade.

3 Claims, 1 Drawing Sheet

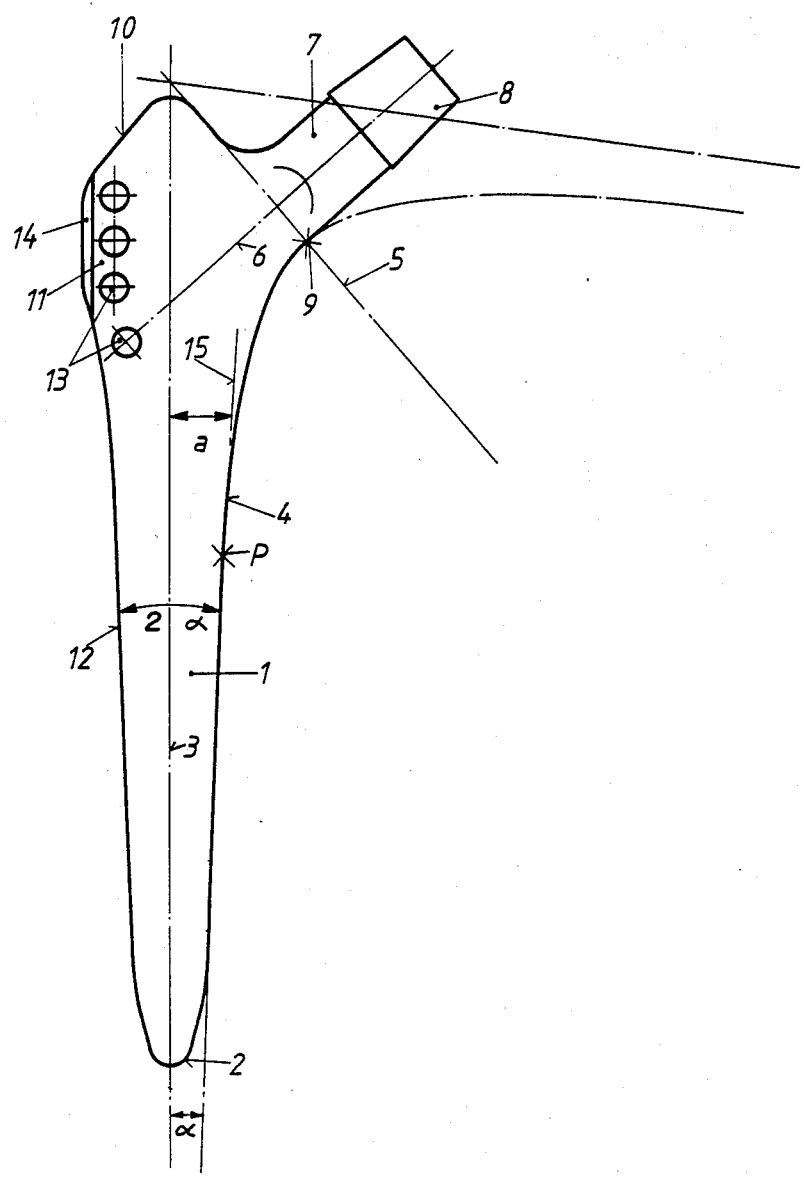

PROSTHESIS FOR A HIP JOINT

This is a continuation of application Ser. No. 032,329 filed Mar. 30, 1987, now abandoned.

This invention relates to a prosthesis for a hip joint. More particularly, this invention relates to a bladelike prosthesis for implanting in a femur.

As is known, various types of blade-like prosthesis have been known for implanting in a femur. In many cases, these prostheses have been provided with a blade-like shaft which expands conically on all sides from a distal free end relative to a longitudinal center line. In addition, it has been known that the medial narrow side of such prostheses frequently continue from the conical part on a continuously curved arc which terminates at the intersection of a prosthesis neck with the blade-like shaft. Examples of such prostheses are described in U.S. Pat. Nos. 4,404,993 and 4,310,931.

Up to the present, the above types of prostheses have usually had the medial narrow side continue in a circular arc to the prosthesis neck. However, a problem arises if the anchoring of the blade-like shaft of such a prosthesis is performed in the area of the diaphysis, that is, in the distal part. Specifically, it is usually necessary to allow the shaft to "settle" for some time after implantation so that the shaft becomes firmly wedged in the femur through a deeper penetration. However, where the medial narrow side is formed on a circular arc, the danger exists that these prostheses come to rest at the distal end of the calcar against the cortex in such a way that deeper penetration is prevented.

Accordingly, it is an object of the invention to improve the adaptation of a hip joint prosthesis to the calcar arc.

It is another object of the invention to avoid butting of a shaft of a prosthesis against the distal end of a calcar.

Briefly, the invention provides a prosthesis for a hip joint which is comprised of a neck and a blade having a distal section of conical shape extending along a longitudinal axis on a predetermined conical angle and a proximal section connected to the neck along a boundary plane disposed in angular relation to the longitudinal axis. In accordance with the invention, a medial narrow side of the proximal section extends from a first point on the distal section on a hyperbolic arc having a vertex at a point of intersection of the boundary plane with the neck.

In addition, the medial narrow side is shaped so that a tangent to the hyperbolic arc at the piont of merger with the distal section forms an angle with the longitudinal axis which is equal to one-half of the conical anglee.

The proximal section of the prosthesis may also have a trochanter wing opposite the medial narrow side, a shoulder extending between the wing and the neck and a lateral narrow side extending from the distal section to the wing.

With the hyperbola shape, the prosthesis has an improved adaptation of the medial blade area to the course of the calcar arc. In particular, butting of the blade against the distal end of the calcar is avoided.

These and other objects and advantages of the invention will become more apparent from the following description taken in conjunction with the accompanying DRAWING wherein:

The DRAWING schematically illustrates an anterior/posterior view of a prosthesis constructed in accordance with the invention.

Referring to the DRAWING, the prosthesis is constructed for use in a hip joint. As illustrated, the prosthesis has a blade 1 formed of a distal section of conical shape which extends from a distal end 2 along a longitudinal axis 3 on a predetermined conical angle $2\alpha$ from lateral to medial, as shown, such that the distal section is symmetrical to the longitudinal axis 3.

The blade 1 also has a proximal section which extends from the distal section and is connected to a neck 7 along a boundary plane 5 disposed in angular relation to the longitudinal axis 3 and perpendicular to the axis 6 of the neck 7.

The neck 7 of the prosthesis carries a conical peg 8 on which a spherical joint head (not shown) can be mounted in known manner.

As illustrated, a medial narrow side 4 of the proximal section extends from a point P on the distal section on a hyperbolic arc having a vertex at a point of intersection 9 of the arc with the boundary plane 5, that is, at the point of intersection of the neck 7 with the boundary plane 5. Further, the hyperbola continues into the distal section at the point P so that the tangent 15 to the arc at the point P forms an angle $\alpha$ with the longitudinal axis 3 equal to one-half of the conical angle of the distal section.

Since the arc of the medial narrow section 4 is a hyperbola, the transverse distance a between the longitudinal axis 3 and the medial narrow side 4 decreases in the distal direction slower than if the arc were a circular arc. As a result, an improved adaptation of the shape of the blade to the anatomical structures in the area of the calcar arc (not shown) is achieved.

As illustrated, the proximal section also has a roof-ridge shaped shoulder 10 extending from the boundary plane 5 to a trochanater wing which is opposite the medial narrow side 4. The lateral narrow side 12 tapers conically from the wing 11 to the distal end of the blade 1. In addition, the wing 11 may contain perforations or openings 13 for identifying the prosthesis and/or for radiographic observation of the bone structure. The outer end of the trochanter wing 11 may also have a tapered area 14.

The invention thus provides a prosthesis for a hip joint which is of relatively simple construction and one in which improved adaptation of the blade area to the course of the calcar arc can be obtained. Further, butting of the blade 1 against the distal end of the calcar (not shown) can be avoided.

What is claimed is:

1. A prosthesis for a hip joint comprising
   a neck; and
   a blade having a distal section of conical shape extending along a longitudinal axis on a predetermined conical angle and a proximal section connected to said neck along a boundary plane disposed in angular relation to said longitudinal axis, said proximal section having a medial narrow side extending on a hyperbolic arc from a first point on said distal section to a second point on said boundary plane, said hyperbolic arc having a vertex at said second point whereby said medial side is adapted to a course of a calcar arc to avoid butting of said blade against a distal end of a calcar and wherein a tangent to said hyperbolic arc at said first point forms an angle with said longitudinal axis equal to one-half of said conical angle.

2. A prosthesis as set forth in claim 1 wherein said proximal section has a trochanter wing opposite said medial narrow side, a shoulder extending between said wing and said neck and a lateral narrow side extending from said distal section to said wing.

3. A prosthesis as set forth in claim 1 wherein said neck carries a conical peg for mounting of a spherical head thereon.

* * * * *

UNITED STATES PATENT AND TRADEMARK OFFICE
CERTIFICATE OF CORRECTION

PATENT NO. : 4,908,035

DATED : March 13, 1990

INVENTOR(S) : ANDRE G. DECKNER, et al

It is certified that error appears in the above-identified patent and that said Letters Patent is hereby corrected as shown below:

Column 1, line 9 "prosthesis" should be -prostheses-
Column 1, line 54-55 "anglee" should be -angle- Signed and Sealed this Twenty-eighth Day of May, 1991

Attest:

HARRY F. MANBECK, JR.

Attesting Officer

Commissioner of Patents and Trademarks